United States Patent
Newman (10) Patent No.: US 9,259,343 B2
(45) Date of Patent: Feb. 16, 2016

(54) DEVICE FOR MITIGATING PLANTAR FASCIITIS

(71) Applicant: Bradley R. Newman, Mundelein, IL (US)

(72) Inventor: Bradley R. Newman, Mundelein, IL (US)

(73) Assignee: Newman Technologies LLC, Mundelein, IL (US)

(*) Notice: Subject to any disclaimer, the term of this patent is extended or adjusted under 35 U.S.C. 154(b) by 303 days.

(21) Appl. No.: 13/833,981

(22) Filed: Mar. 15, 2013

(65) Prior Publication Data

US 2014/0012173 A1 Jan. 9, 2014

Related U.S. Application Data

(60) Provisional application No. 61/669,005, filed on Jul. 6, 2012.

(51) Int. Cl.
*A61F 5/01* (2006.01)

(52) U.S. Cl.
CPC ............. *A61F 5/0127* (2013.01); *A61F 5/0111* (2013.01)

(58) Field of Classification Search
CPC .... A43B 13/183; A43B 13/181; A43B 21/30; A43B 13/14; A43B 13/182; A43B 13/187; A43B 13/189; A43B 1/0054; A43B 3/0005; A43B 13/203; A43B 7/1415; A43B 7/142; A43B 7/1425; A43B 7/1435
USPC ...................................... 602/23–28; 128/882
See application file for complete search history.

(56) References Cited

U.S. PATENT DOCUMENTS

| | | | |
|---|---|---|---|
| 1,301,491 A | | 4/1919 | Nelson |
| 2,439,100 A | * | 4/1948 | Richards ........................ 602/28 |
| 3,527,209 A | | 9/1970 | Baker |
| 3,589,359 A | | 6/1971 | Hill |
| 3,673,189 A | | 6/1972 | Curran et al. |
| 3,754,339 A | | 8/1973 | Terasaki |
| 3,861,398 A | | 1/1975 | Leydecker |
| 3,920,835 A | | 11/1975 | Van Scott et al. |
| 3,984,566 A | | 10/1976 | Van Scott et al. |
| 3,985,853 A | | 10/1976 | Weisberg |
| 3,988,470 A | | 10/1976 | Van Scott et al. |
| 4,007,420 A | | 2/1977 | Halek et al. |
| 4,139,337 A | | 2/1979 | David et al. |
| 4,159,111 A | | 6/1979 | Lowth |
| 4,179,826 A | | 12/1979 | Davidson |
| 4,180,058 A | | 12/1979 | Brem |
| 4,192,297 A | | 3/1980 | Labrecque |

(Continued)

FOREIGN PATENT DOCUMENTS

WO 2011080705 A1 7/2011

OTHER PUBLICATIONS

Tong & Furia, "Economic Burden of Plantar Fasciitis Treatment in the United States"; Am J Orthop. 2010; 39(5): 227-231.

(Continued)

*Primary Examiner* — Michael Brown
(74) *Attorney, Agent, or Firm* — Richards Patent Law P.C.

(57) ABSTRACT

A device for mitigating plantar fasciitis that includes a truss structure, an upper anchor, and an actuator. The upper anchor is proximally located from the truss structure and the actuator couples a posterior portion of the truss structure to a posterior portion of the upper anchor. The actuator is designed to provide assistive force to urge heel lift during ambulation such that the tension in the plantar fascia is reduced.

22 Claims, 4 Drawing Sheets

(56) References Cited

U.S. PATENT DOCUMENTS

| | | |
|---|---|---|
| 4,194,007 A | 3/1980 | Van Scott et al. |
| 4,213,208 A | 7/1980 | Marne |
| 4,222,182 A | 9/1980 | Sears |
| 4,224,339 A | 9/1980 | Van Scott et al. |
| 4,267,728 A | 5/1981 | Manley et al. |
| 4,283,386 A | 8/1981 | Van Scott et al. |
| 4,325,367 A | 4/1982 | Tapper |
| 4,363,815 A | 12/1982 | Yu et al. |
| 4,392,487 A | 7/1983 | Selner et al. |
| 4,413,430 A | 11/1983 | Brown |
| 4,422,453 A | 12/1983 | Salort |
| 4,439,934 A | 4/1984 | Brown |
| 4,446,580 A | 5/1984 | Furuya et al. |
| 4,452,447 A | 6/1984 | Lepley et al. |
| 4,461,288 A | 7/1984 | Curtis |
| 4,472,890 A | 9/1984 | Gilbert |
| 4,503,576 A | 3/1985 | Brown |
| 4,510,700 A | 4/1985 | Brown |
| 4,520,580 A | 6/1985 | Brown |
| 4,538,595 A | 9/1985 | Hajianpour |
| 4,554,912 A | 11/1985 | Haberman |
| 4,600,016 A | 7/1986 | Boyd et al. |
| 4,614,179 A | 9/1986 | Gardner et al. |
| 4,614,180 A | 9/1986 | Gardner et al. |
| 4,620,698 A | 11/1986 | Reed et al. |
| 4,633,877 A | 1/1987 | Pendergast |
| 4,649,939 A | 3/1987 | Curtis |
| 4,653,748 A | 3/1987 | Seel et al. |
| 4,662,079 A | 5/1987 | Graf et al. |
| 4,663,865 A | 5/1987 | Telecemian |
| 4,667,423 A | 5/1987 | Autry et al. |
| 4,669,142 A | 6/1987 | Meyer |
| 4,686,994 A | 8/1987 | Harr et al. |
| 4,696,289 A | 9/1987 | Gardner et al. |
| 4,702,232 A | 10/1987 | Gardner et al. |
| 4,716,662 A | 1/1988 | Bar |
| 4,718,913 A | 1/1988 | Voisin |
| 4,721,101 A | 1/1988 | Gardner et al. |
| 4,735,195 A | 4/1988 | Blum et al. |
| 4,747,410 A | 5/1988 | Cohen |
| RE32,698 E | 6/1988 | Brown |
| 4,753,228 A | 6/1988 | Selner et al. |
| 4,756,096 A | 7/1988 | Meyer |
| 4,759,542 A | 7/1988 | Hudec |
| 4,767,333 A | 8/1988 | Born |
| 4,771,768 A | 9/1988 | Crispin |
| 4,782,827 A | 11/1988 | Paratte |
| 4,803,747 A | 2/1989 | Brown |
| 4,807,874 A | 2/1989 | Little |
| 4,823,799 A | 4/1989 | Robbins |
| RE32,939 E | 6/1989 | Gardner et al. |
| RE32,940 E | 6/1989 | Gardner et al. |
| 4,856,496 A | 8/1989 | Chursinoff |
| 4,910,889 A | 3/1990 | Bonaventure et al. |
| 4,915,406 A | 4/1990 | Graillat |
| 4,928,988 A | 5/1990 | Hue |
| 4,938,777 A | 7/1990 | Mason et al. |
| 4,955,370 A | 9/1990 | Pettine |
| 4,974,343 A | 12/1990 | Davidson |
| 5,017,587 A | 5/1991 | Montes |
| 5,020,523 A | 6/1991 | Bodine |
| 5,020,525 A | 6/1991 | Ewing et al. |
| RE33,648 E | 7/1991 | Brown |
| 5,036,851 A | 8/1991 | Cohen |
| 5,044,360 A | 9/1991 | Janke |
| 5,045,559 A | 9/1991 | Scott |
| 5,056,507 A | 10/1991 | Yum |
| 5,058,585 A | 10/1991 | Kendall et al. |
| 5,062,859 A | 11/1991 | Naeder |
| 5,069,212 A | 12/1991 | Cohen |
| 5,088,757 A | 2/1992 | Hauglin |
| 5,094,445 A | 3/1992 | Winkelvoss |
| 5,099,860 A | 3/1992 | Amrein |
| 5,112,356 A | 5/1992 | Harris et al. |
| 5,129,395 A | 7/1992 | Hoffmann |
| 5,150,716 A | 9/1992 | Franssen et al. |
| 5,151,415 A | 9/1992 | Sirany |
| 5,170,572 A | 12/1992 | Kantro |
| 5,177,885 A | 1/1993 | Marmonnier |
| 5,181,332 A | 1/1993 | Uren et al. |
| 5,197,932 A | 3/1993 | Smith, IV |
| 5,215,508 A | 6/1993 | Bastow |
| 5,230,700 A | 7/1993 | Humbert et al. |
| 5,253,659 A | 10/1993 | McNamara et al. |
| 5,263,473 A | 11/1993 | McWhorter |
| 5,267,924 A | 12/1993 | Miller et al. |
| 5,269,290 A | 12/1993 | Barrett et al. |
| 5,282,328 A | 2/1994 | Peterson |
| 5,297,540 A | 3/1994 | Kaiser et al. |
| 5,306,230 A | 4/1994 | Bodine |
| 5,311,680 A | 5/1994 | Comparetto |
| 5,323,549 A | 6/1994 | Segel et al. |
| 5,323,765 A | 6/1994 | Brown |
| 5,352,185 A | 10/1994 | Blauth et al. |
| 5,354,260 A | 10/1994 | Cook |
| 5,368,536 A | 11/1994 | Stodgell |
| 5,379,530 A | 1/1995 | Bell et al. |
| 5,387,384 A | 2/1995 | Irving |
| 5,394,626 A | 3/1995 | Brown |
| 5,399,155 A | 3/1995 | Strassburg et al. |
| 5,400,529 A | 3/1995 | Bell et al. |
| 5,404,659 A | 4/1995 | Burke et al. |
| 5,418,253 A | 5/1995 | Cavazza et al. |
| 5,421,798 A | 6/1995 | Bond et al. |
| 5,429,117 A | 7/1995 | McNamara et al. |
| 5,443,440 A | 8/1995 | Tumey et al. |
| 5,445,602 A | 8/1995 | Grim et al. |
| 5,486,157 A | 1/1996 | DiBenedetto |
| 5,494,924 A | 2/1996 | Cavazza et al. |
| 5,499,460 A | 3/1996 | Bryant et al. |
| 5,520,628 A | 5/1996 | Wehr |
| 5,529,075 A | 6/1996 | Clark |
| 5,573,501 A | 11/1996 | Ruscito et al. |
| 5,578,051 A | 11/1996 | Mirza |
| 5,584,798 A | 12/1996 | Fox |
| 5,586,564 A | 12/1996 | Barrett et al. |
| 5,607,756 A | 3/1997 | Yamauchi et al. |
| 5,611,153 A | 3/1997 | Fisher et al. |
| 5,614,556 A | 3/1997 | Cavazza et al. |
| 5,620,413 A | 4/1997 | Olson |
| 5,620,446 A | 4/1997 | McNamara et al. |
| 5,627,212 A | 5/1997 | Cavazza et al. |
| 5,639,767 A | 6/1997 | Cavazza et al. |
| 5,645,516 A | 7/1997 | Foster |
| 5,650,066 A | 7/1997 | Blandin et al. |
| 5,669,872 A | 9/1997 | Fox |
| 5,678,566 A | 10/1997 | Dribbon |
| 5,695,526 A | 12/1997 | Wilson |
| 5,702,354 A | 12/1997 | DeSpain et al. |
| 5,718,673 A | 2/1998 | Shipstead |
| 5,722,186 A | 3/1998 | Brown |
| 5,727,271 A | 3/1998 | Romanato et al. |
| 5,749,668 A | 5/1998 | McIlvain et al. |
| 5,772,945 A | 6/1998 | Brown |
| 5,776,090 A | 7/1998 | Bergmann et al. |
| 5,790,998 A | 8/1998 | Crescimbeni |
| 5,794,361 A | 8/1998 | Sadler |
| 5,799,659 A | 9/1998 | Stano |
| 5,800,570 A | 9/1998 | Collier |
| 5,826,585 A | 10/1998 | Franssen et al. |
| 5,834,513 A | 11/1998 | Ptchelintsev et al. |
| 5,840,053 A | 11/1998 | Roth |
| 5,842,294 A | 12/1998 | Fabricant |
| 5,847,003 A | 12/1998 | Ptchelintsev et al. |
| 5,865,781 A * | 2/1999 | Lieber et al. .................... 602/32 |
| 5,867,837 A | 2/1999 | Otto et al. |
| 5,887,591 A | 3/1999 | Powell et al. |
| 5,891,002 A | 4/1999 | Maki |
| 5,894,687 A | 4/1999 | Lin |
| 5,897,464 A | 4/1999 | Mcleod |
| 5,897,520 A | 4/1999 | Gerig |
| 5,902,609 A | 5/1999 | Lee |
| 5,913,901 A | 6/1999 | Lacroix |
| 5,921,243 A | 7/1999 | Shakoor |

(56) References Cited

U.S. PATENT DOCUMENTS

| | | | |
|---|---|---|---|
| 5,941,835 | A | 8/1999 | Sundman |
| 5,944,679 | A | 8/1999 | DeToro |
| 5,945,116 | A | 8/1999 | Haque et al. |
| 5,962,018 | A | 10/1999 | Curtis et al. |
| 5,984,915 | A | 11/1999 | Loeb et al. |
| 6,000,082 | A | 12/1999 | Nguyen |
| 6,010,468 | A | 1/2000 | Grove et al. |
| 6,019,741 | A | 2/2000 | Prieskorn |
| 6,021,589 | A | 2/2000 | Cagliari et al. |
| 6,032,296 | A | 3/2000 | Kelly et al. |
| 6,050,004 | A | 4/2000 | Miralles et al. |
| 6,059,744 | A | 5/2000 | Hardt |
| 6,060,083 | A | 5/2000 | Dorr et al. |
| 6,065,767 | A | 5/2000 | Girotto et al. |
| 6,066,624 | A | 5/2000 | Woo et al. |
| 6,069,169 | A | 5/2000 | Ptchelintsev et al. |
| 6,071,962 | A | 6/2000 | Ptchelintsev et al. |
| 6,074,414 | A | 6/2000 | Haas et al. |
| 6,090,050 | A | 7/2000 | Constantinides |
| 6,092,314 | A | 7/2000 | Rothbart |
| 6,110,078 | A | 8/2000 | Dyer |
| 6,125,557 | A | 10/2000 | Brown |
| 6,127,393 | A | 10/2000 | Fernandez-Pol |
| 6,132,756 | A | 10/2000 | Haque et al. |
| 6,141,889 | A | 11/2000 | Baum |
| 6,148,546 | A | 11/2000 | Demarchi |
| 6,149,577 | A | 11/2000 | Bouldin et al. |
| 6,159,485 | A | 12/2000 | Yu et al. |
| 6,160,264 | A | 12/2000 | Rebiere |
| 6,173,452 | B1 | 1/2001 | Kelly et al. |
| 6,176,854 | B1 | 1/2001 | Cone |
| 6,217,860 | B1 | 4/2001 | Woo et al. |
| 6,224,521 | B1 | 5/2001 | Foucault |
| 6,228,044 | B1 | 5/2001 | Jensen et al. |
| 6,228,045 | B1 | 5/2001 | Gaylord et al. |
| 6,251,088 | B1 | 6/2001 | Kaufman et al. |
| 6,257,613 | B1 | 7/2001 | Porte |
| 6,267,742 | B1 | 7/2001 | Krivosha et al. |
| 6,277,057 | B1 | 8/2001 | Hayden |
| 6,283,897 | B1 | 9/2001 | Patton |
| 6,301,807 | B1 | 10/2001 | Gardiner |
| 6,314,584 | B1 | 11/2001 | Errera |
| 6,315,786 | B1 | 11/2001 | Smuckler |
| 6,319,215 | B1 | 11/2001 | Manor et al. |
| 6,322,096 | B2 | 11/2001 | Porte |
| 6,333,356 | B1 | 12/2001 | Ptchelintsev et al. |
| 6,334,854 | B1 | 1/2002 | Davis |
| 6,335,023 | B1 | 1/2002 | Yu et al. |
| 6,350,246 | B1 | 2/2002 | DeToro et al. |
| 6,358,219 | B1 | 3/2002 | Arkans |
| 6,367,172 | B2 | 4/2002 | Hernandez |
| 6,368,292 | B1 | 4/2002 | Ogden et al. |
| 6,379,321 | B2 | 4/2002 | Gaylord et al. |
| 6,393,736 | B1 | 5/2002 | Greer, Jr. et al. |
| 6,398,740 | B1 | 6/2002 | Lavery et al. |
| 6,402,788 | B1 | 6/2002 | Wood et al. |
| 6,406,706 | B1 | 6/2002 | Haque et al. |
| 6,408,544 | B1 | 6/2002 | Hernandez |
| 6,410,570 | B1 | 6/2002 | Fernandez-Pol |
| 6,425,843 | B1 | 7/2002 | Storfer et al. |
| 6,430,831 | B1 | 8/2002 | Sundman |
| 6,443,995 | B1 | 9/2002 | Townsend et al. |
| 6,454,733 | B1 | 9/2002 | Krusenklaus |
| 6,457,263 | B1 | 10/2002 | Rudy |
| 6,463,612 | B1 | 10/2002 | Potter |
| 6,463,679 | B1 | 10/2002 | Buttigieg |
| 6,464,659 | B1 | 10/2002 | DeToro et al. |
| 6,485,661 | B1 | 11/2002 | Brown |
| 6,492,398 | B1 | 12/2002 | Vyas |
| 6,493,958 | B1 | 12/2002 | Tadin |
| 6,499,485 | B1 | 12/2002 | Pepera |
| 6,524,593 | B1 | 2/2003 | Yu et al. |
| 6,558,339 | B1 | 5/2003 | Graham |
| 6,562,075 | B2 | 5/2003 | Townsend et al. |
| 6,573,282 | B1 | 6/2003 | Yaksh et al. |
| 6,592,534 | B1 | 7/2003 | Rutt et al. |
| 6,593,371 | B1 | 7/2003 | Staggs |
| 6,594,922 | B1 | 7/2003 | Mansfield et al. |
| 6,595,904 | B1 | 7/2003 | Staffa |
| 6,602,216 | B1 | 8/2003 | Nordt, III |
| 6,615,080 | B1 | 9/2003 | Unsworth et al. |
| 6,616,619 | B2 | 9/2003 | Fusco |
| 6,620,818 | B1 | 9/2003 | Davis |
| 6,624,171 | B1 | 9/2003 | Harris et al. |
| 6,625,897 | B2 | 9/2003 | Tadin |
| 6,632,187 | B2 | 10/2003 | Bak |
| 6,641,550 | B1 | 11/2003 | Johnson |
| 6,648,843 | B1 | 11/2003 | Marciano et al. |
| 6,681,403 | B2 | 1/2004 | Lyden |
| 6,682,497 | B2 | 1/2004 | Jensen et al. |
| 6,694,648 | B2 | 2/2004 | Eriksen |
| 6,695,797 | B2 * | 2/2004 | Trieloff .................... 601/27 |
| 6,699,209 | B2 | 3/2004 | Turtzo |
| 6,699,295 | B2 | 3/2004 | Lee et al. |
| 6,710,083 | B2 | 3/2004 | Parks |
| 6,714,012 | B2 | 3/2004 | Belt et al. |
| 6,732,457 | B2 | 5/2004 | Gardiner |
| 6,740,327 | B2 | 5/2004 | Yu et al. |
| 6,743,260 | B2 | 6/2004 | Townsend et al. |
| 6,745,501 | B2 | 6/2004 | Brown |
| 6,748,676 | B1 | 6/2004 | Chenevert |
| 6,767,330 | B2 | 7/2004 | Lavery et al. |
| 6,767,332 | B1 | 7/2004 | Pardue et al. |
| 6,790,193 | B2 | 9/2004 | Wellershaus et al. |
| 6,793,636 | B1 | 9/2004 | Pepera |
| 6,804,571 | B2 | 10/2004 | Fullen et al. |
| 6,808,716 | B2 | 10/2004 | Yu et al. |
| 6,815,439 | B2 | 11/2004 | Harris et al. |
| 6,821,523 | B2 | 11/2004 | Maibach et al. |
| 6,823,550 | B2 | 11/2004 | Kantro |
| 6,824,786 | B2 | 11/2004 | Yu et al. |
| 6,836,744 | B1 | 12/2004 | Asphahani et al. |
| 6,886,276 | B2 | 5/2005 | Hlavac |
| 6,889,088 | B2 | 5/2005 | Demian |
| 6,889,452 | B2 | 5/2005 | Ailey et al. |
| 6,918,883 | B2 | 7/2005 | Horton et al. |
| 6,922,919 | B2 | 8/2005 | Chenevert |
| 6,926,739 | B1 | 8/2005 | O'Connor et al. |
| 6,938,362 | B2 | 9/2005 | Saillet et al. |
| 6,945,946 | B2 | 9/2005 | Rooney |
| 6,974,431 | B2 | 12/2005 | Jensen et al. |
| D514,225 | S | 1/2006 | Sassi |
| 6,981,856 | B2 | 1/2006 | Graf et al. |
| 6,998,247 | B2 | 2/2006 | Monfre et al. |
| 7,017,218 | B2 | 3/2006 | Nguyen |
| 7,018,352 | B2 | 3/2006 | Pressman et al. |
| 7,019,000 | B1 | 3/2006 | Bernard et al. |
| 7,039,446 | B2 | 5/2006 | Ruchti et al. |
| 7,041,075 | B2 | 5/2006 | Sullivan |
| 7,060,684 | B1 | 6/2006 | Quijano et al. |
| 7,068,379 | B2 | 6/2006 | Sundman et al. |
| 7,115,106 | B2 | 10/2006 | Bodenschatz et al. |
| 7,117,034 | B2 | 10/2006 | Kronberg |
| 7,124,518 | B1 | 10/2006 | Brown |
| 7,125,509 | B1 | 10/2006 | Smith |
| 7,133,710 | B2 | 11/2006 | Acosta et al. |
| 7,137,998 | B2 | 11/2006 | Bedard |
| 7,147,667 | B2 | 12/2006 | Bedard |
| 7,165,916 | B2 | 1/2007 | Nanayakkara |
| 7,179,206 | B2 | 2/2007 | Backes et al. |
| 7,192,410 | B1 | 3/2007 | Rodgers |
| 7,199,131 | B2 | 4/2007 | Lindstrom |
| 7,206,718 | B2 | 4/2007 | Cavanagh et al. |
| 7,207,126 | B2 | 4/2007 | Gantier |
| 7,214,202 | B1 | 5/2007 | Vogel et al. |
| 7,226,485 | B2 | 6/2007 | Townsend et al. |
| 7,231,728 | B2 | 6/2007 | Darby |
| 7,250,046 | B1 | 7/2007 | Fallat |
| 7,264,604 | B1 | 9/2007 | Schuren et al. |
| 7,287,340 | B2 | 10/2007 | Talbott |
| 7,299,080 | B2 | 11/2007 | Acosta et al. |
| 7,316,083 | B2 | 1/2008 | Labonte |
| 7,325,813 | B2 | 2/2008 | Bock |
| 7,335,177 | B2 | 2/2008 | Reynolds et al. |

(56) References Cited

U.S. PATENT DOCUMENTS

| | | |
|---|---|---|
| 7,335,178 B2 | 2/2008 | Berger et al. |
| 7,337,680 B2 | 3/2008 | Kantro |
| 7,354,384 B2 | 4/2008 | Martin et al. |
| 7,368,456 B2 | 5/2008 | Ford |
| 7,374,569 B2 | 5/2008 | Whatcott et al. |
| 7,381,192 B2 | 6/2008 | Brodard et al. |
| 7,392,559 B2 | 7/2008 | Peterson |
| 7,430,820 B2 | 10/2008 | Andreoli et al. |
| 7,451,991 B2 | 11/2008 | Labonte |
| 7,507,259 B2 | 3/2009 | Townsend et al. |
| 7,540,987 B1 | 6/2009 | Graf et al. |
| 7,549,232 B2 | 6/2009 | Tadin |
| 7,552,494 B2 | 6/2009 | Peterson |
| 7,569,023 B2 | 8/2009 | Dobbs |
| 7,572,241 B2 | 8/2009 | Slautterback et al. |
| 7,578,852 B2 | 8/2009 | Townsend et al. |
| 7,608,258 B2 | 10/2009 | Mishra |
| 7,611,543 B2 | 11/2009 | Townsend et al. |
| 7,621,877 B2 | 11/2009 | Schnall |
| 7,624,519 B1 | 12/2009 | Thorne |
| 7,625,349 B2 | 12/2009 | Bleau |
| 7,637,034 B2 | 12/2009 | Ailey et al. |
| 7,662,829 B2 | 2/2010 | Ford |
| 7,685,728 B2 | 3/2010 | Goonetilleke et al. |
| RE41,278 E | 4/2010 | Yu et al. |
| 7,690,132 B2 | 4/2010 | Wilkenfeld |
| 7,691,076 B2 | 4/2010 | Castro |
| 7,694,437 B2 | 4/2010 | Hogan |
| RE41,339 E | 5/2010 | Yu et al. |
| 7,712,173 B2 | 5/2010 | Labonte |
| 7,718,674 B2 | 5/2010 | Aberg |
| 7,727,173 B2 | 6/2010 | Rooney |
| 7,727,174 B2 | 6/2010 | Chang et al. |
| 7,753,864 B2 | 7/2010 | Beckwith et al. |
| 7,756,585 B2 | 7/2010 | Embrey et al. |
| 7,758,529 B2 | 7/2010 | Jensen et al. |
| 7,765,719 B2 | 8/2010 | Nurse et al. |
| 7,789,027 B1 | 9/2010 | Marshall |
| 7,789,841 B2 | 9/2010 | Huckle et al. |
| 7,793,666 B2 | 9/2010 | Weinfield |
| 7,806,844 B2 | 10/2010 | Outred et al. |
| 7,812,030 B2 | 10/2010 | Ford |
| 7,823,238 B2 | 11/2010 | Din Mahamed |
| D629,913 S | 12/2010 | Beckwith et al. |
| 7,849,609 B2 | 12/2010 | Edington et al. |
| 7,854,071 B2 | 12/2010 | Goonetilleke et al. |
| 7,854,929 B2 | 12/2010 | Badalemente et al. |
| 7,857,742 B2 | 12/2010 | Wang |
| 7,867,184 B2 | 1/2011 | Mitchell |
| 7,867,284 B2 | 1/2011 | Bedard |
| 7,874,996 B2 | 1/2011 | Weinstein et al. |
| 7,875,229 B2 | 1/2011 | Wright et al. |
| D631,971 S | 2/2011 | Turtzo et al. |
| 7,918,813 B2 | 4/2011 | Drake et al. |
| 7,922,681 B2 | 4/2011 | Berger et al. |
| 7,926,363 B2 | 4/2011 | Miller et al. |
| 7,942,935 B2 | 5/2011 | Iversen et al. |
| 7,947,004 B2 | 5/2011 | Kazerooni et al. |
| 7,950,163 B2 | 5/2011 | Lo |
| 7,951,097 B2 | 5/2011 | Schaeffer |
| 7,967,768 B2 | 6/2011 | Watts |
| 7,972,290 B1 | 7/2011 | Chisholm |
| 7,973,046 B2 | 7/2011 | Rodemer |
| 7,988,602 B1 | 8/2011 | Janzen |
| 8,002,682 B2 | 8/2011 | Dye |
| 8,007,456 B2 | 8/2011 | Stano |
| 8,008,345 B2 | 8/2011 | West et al. |
| 8,019,423 B2 | 9/2011 | Possover |
| 8,021,317 B2 | 9/2011 | Arnold et al. |
| 8,021,367 B2 | 9/2011 | Bourke et al. |
| 8,026,267 B2 | 9/2011 | Rozencweig et al. |
| 8,027,717 B2 | 9/2011 | Storm |
| RE42,902 E | 11/2011 | Yu et al. |
| 8,048,012 B1 | 11/2011 | Castro |
| 8,048,423 B2 | 11/2011 | First |
| 8,051,582 B2 | 11/2011 | Nurse et al. |
| 8,057,410 B2 | 11/2011 | Angold et al. |
| 8,062,243 B2 | 11/2011 | DeToro et al. |
| 8,075,501 B2 | 12/2011 | Miller et al. |
| 8,075,633 B2 | 12/2011 | Herr et al. |
| 8,075,634 B2 | 12/2011 | Hurowitz |
| 8,083,703 B2 | 12/2011 | Daizade |
| 8,083,807 B2 | 12/2011 | Auberger et al. |
| 8,092,356 B2 | 1/2012 | Seel et al. |
| 8,109,014 B2 | 2/2012 | Miller et al. |
| 8,119,109 B2 | 2/2012 | Tamarkin et al. |
| 8,313,451 B2 | 11/2012 | Cox |
| 8,556,839 B2 * | 10/2013 | Caldwell et al. ............... 602/16 |
| 8,900,171 B2 * | 12/2014 | Darby et al. .................. 602/16 |
| 2005/0131324 A1 | 6/2005 | Bledsoe |
| 2007/0100268 A1 | 5/2007 | Fisher et al. |
| 2008/0154166 A1 | 6/2008 | Beckwith et al. |
| 2010/0324461 A1 | 12/2010 | Darby, II et al. |
| 2011/0082403 A1 | 4/2011 | Hill |
| 2011/0172578 A1 | 7/2011 | Chiu et al. |
| 2012/0065564 A1 | 3/2012 | Hoffmeier |
| 2012/0253244 A1 | 10/2012 | Femano et al. |
| 2013/0046218 A1 | 2/2013 | Wiggin et al. |

OTHER PUBLICATIONS

Toad Corporation, "Mobility: TBrace"; http://www.toadcorporation.com/; 2010; 1; Reno, Nevada.

US 8,298,166, Oct. 2012, Hoffmeier et al. (withdrawn).

International Search Report and Written Opinion for International Application No. PCT/EP2014/014767, issued May 6, 2014, Applicant, Newman Technologies LLC. (15 pages).

* cited by examiner

DEVICE FOR MITIGATING PLANTAR FASCIITIS

CROSS-REFERENCE TO RELATED APPLICATIONS

This application incorporates by reference and claims priority to U.S. Provisional Application No. 61/669,005 filed on Jul. 6, 2012.

BACKGROUND OF THE INVENTION

The present subject matter relates generally to an orthotic device that mitigates and treats plantar fasciitis.

The plantar fascia is a fibrous band within the foot that extends from the bottom of the heel bone to each of the toes. When a person stands, the plantar fascia is stretched under the load of a person's weight, an effect known as the "bowstring effect." Once stabilized against the ground, the windlass action of a normal plantar fascia will cause the heel to lift and invert. As the metatarsals and ankle are dorsiflexed during ambulation, the plantar fascia is stretched even further. As such, the plantar fascia is under the greatest tension just as the heel lifts off the ground.

Plantar fasciitis develops when, upon impact, strain, or pressure on the bottom of the foot, the plantar fascia becomes over-stretched and micro-tears develop at its attachment to the heel bone. Plantar fasciitis leads to pain in the plantar fascia upon weight bearing and pressure applied to the bottom of the foot, especially at the point of attachment of the plantar fascia to the heel bone. Any activity that causes the plantar fascia to stretch, such as ambulation, will aggravate the condition.

In severe cases of plantar fasciitis, surgery is performed and requires months of recovery along with prolonged use of custom orthotics to support the plantar fascia during ambulation. Therefore, early treatment of plantar fasciitis is desired to avoid surgery.

Current treatment of plantar fasciitis generally focuses on reducing stress to the plantar fascia through the use of custom orthotic devices, such as custom-made foot arch supports. However, custom-made foot arch supports fail to provide sufficient support to the plantar fascia during ambulation because current orthotics do not prevent hyperextension of the plantar fascia upon push-off. Further, these orthotics are generally expensive because each is custom-made to each user's foot profile.

Footplates, foot braces and orthopedic boots also exist to decrease the tension on the connection of the plantar fascia and the heel. However, these devices completely immobilize the plantar fascia wherein it becomes stiff and inflexible. As a result, when the user eventually does apply weight to the foot, the healed micro tears in the plantar fascia can be reinjured, thereby forfeiting any progress made during recovery. Further, a user's daily activities are substantially hindered, if not completely disrupted, by the constrictive, and typically bulky, nature and design of the foot braces or orthopedic boots.

In addition, the rigidity provided by a footplate, foot brace, or orthopedic boot, may further contribute to an abnormal gait by overcompensating for the injured plantar fascia and actually worsen the condition or create additional orthopedic problems elsewhere in the body.

Accordingly, there is a need for a device to mitigate plantar fasciitis by providing the correct balance of support and freedom of movement to reduce tension in the plantar fascia during ambulation, while at the same time not completely immobilizing the plantar fascia, as described and claimed herein.

BRIEF SUMMARY OF THE INVENTION

The present disclosure provides a device and method for mitigating plantar fasciitis. Various examples of the device and method are provided herein.

In an embodiment, a device that reduces tension in a plantar fascia during ambulation includes a truss structure, an upper anchor, and an actuator. The truss structure includes a posterior portion, a medial portion, a lateral end, and a medial end. The upper anchor is proximally located from the truss structure. The actuator couples the posterior portion of the truss structure to a posterior portion of the upper anchor.

The truss structure may further include at least one stabilizing element that stabilizes the truss structure to a user's shoe during ambulation. In addition, the truss structure may also include at least one securing mechanism that extends from the lateral portion of the truss structure to the medial portion of the truss structure, wherein the securing mechanism secures the truss structure to a user's shoe.

In one example, the securing mechanism includes at least one dorsal strap that extends dorsally from the lateral portion of the truss structure to the medial portion of the truss structure, and at least one ventral strap that extends ventrally from the lateral portion of the truss structure to the medial portion of the truss structure.

The truss structure may be configured such that the lateral end of the truss structure approximately aligns with a lateral metatarsophalangeal joint of a user's foot, and the medial end of the truss structure approximately aligns with a medial metatarsophalangeal joint of a user's foot. Having such alignment, the truss structure may allow mobility of the metatarsophalangeal joint during ambulation.

The truss structure may be attached to the outside of a user's shoe, inserted into a user's shoe, or integrated within the structure of a user's shoe.

In addition, the truss structure may include a heel support to further support the plantar fascia during ambulation.

In one example, the upper anchor is a leg support. The upper anchor may include a connector element to secure the upper anchor to the actuator. The upper anchor may be configured to fit around a portion of a user's leg, including but not limited to, a user's ankle, calf, knee joint, lower thigh, or upper thigh or hip.

The actuator of the device provides tension to urge heel lift during ambulation. The actuator may include non-elastic material, elastic material, a spring, or combination thereof. The actuator may further include a tension sensor and/or a tension adjustment mechanism. In additional contemplated embodiments, the actuator may include an electromechanical actuator.

In an embodiment, the device includes an upper anchor, an attachment point, and an actuator. The upper anchor is adapted to be secured to a user's leg, for example, at a user's ankle, calf, knee, lower thigh or upper thigh or hip. The attachment point is adapted to be secured to the posterior portion of the user's heel. The actuator couples the upper anchor to the attachment point, wherein the actuator pulls the attachment point towards the upper anchor. The attachment point may be integrated into a user's shoe or, alternatively, is a portion of a truss structure adapted to be secured to a user's shoe.

The embodiment described above is merely one example and numerous iterations and variations of the device will be apparent to those skilled in the art based on the teachings provided herein.

The present disclosure also provides for a method of mitigating plantar fasciitis including providing a device disclosed herein, associating a truss structure with a user's shoe, inserting a user's foot into the shoe, and securing an upper anchor to the user, and connecting the truss structure to the upper anchor through an actuator. The actuator is designed to urge heel lift during ambulation.

An advantage of the device provided herein includes protection against hyperextension of the plantar fascia during ambulation.

Another advantage of the device provided herein is that the device allows the plantar fascia to remain mobile while reducing the risk of renewed injury to the plantar fascia, thus speeding the recovery process.

Another advantage of the device provided herein is that the device reduces the amount of work done by a user's foot, thereby benefiting a wide range of users with various foot conditions or whose occupation requires prolonged standing or walking.

A further advantage of the device provided herein is that a user can conveniently use the device in connection with their normal shoe, thus avoiding the purchase of a therapeutic shoe or boot. In addition, the device does not disrupt a user's daily activities, in contrast to a orthopedic boot or foot brace that tends to disrupt a user's normal activities.

Yet another advantage of the device disclosed herein is that the tension provided by the actuator is adjustable. Therefore, as treatment of the plantar fasciitis progresses, less and less tension can be used. In other words, the device creates a smooth transition towards a point in time when essentially no tension is used and the user is fully recovered.

An advantage of the method for mitigating plantar fasciitis provided herein includes a noninvasive treatment option that does not include corticosteroid injections, expensive ultrasound therapy, or using devices that immobilize a user's foot.

Another advantage of the method disclosed herein includes a treatment that reduces the pain associated with plantar fasciitis during ambulation. Further, the method provided herein allows a user to continue with daily activities, even in their own shoes.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figures 1A, 1B:
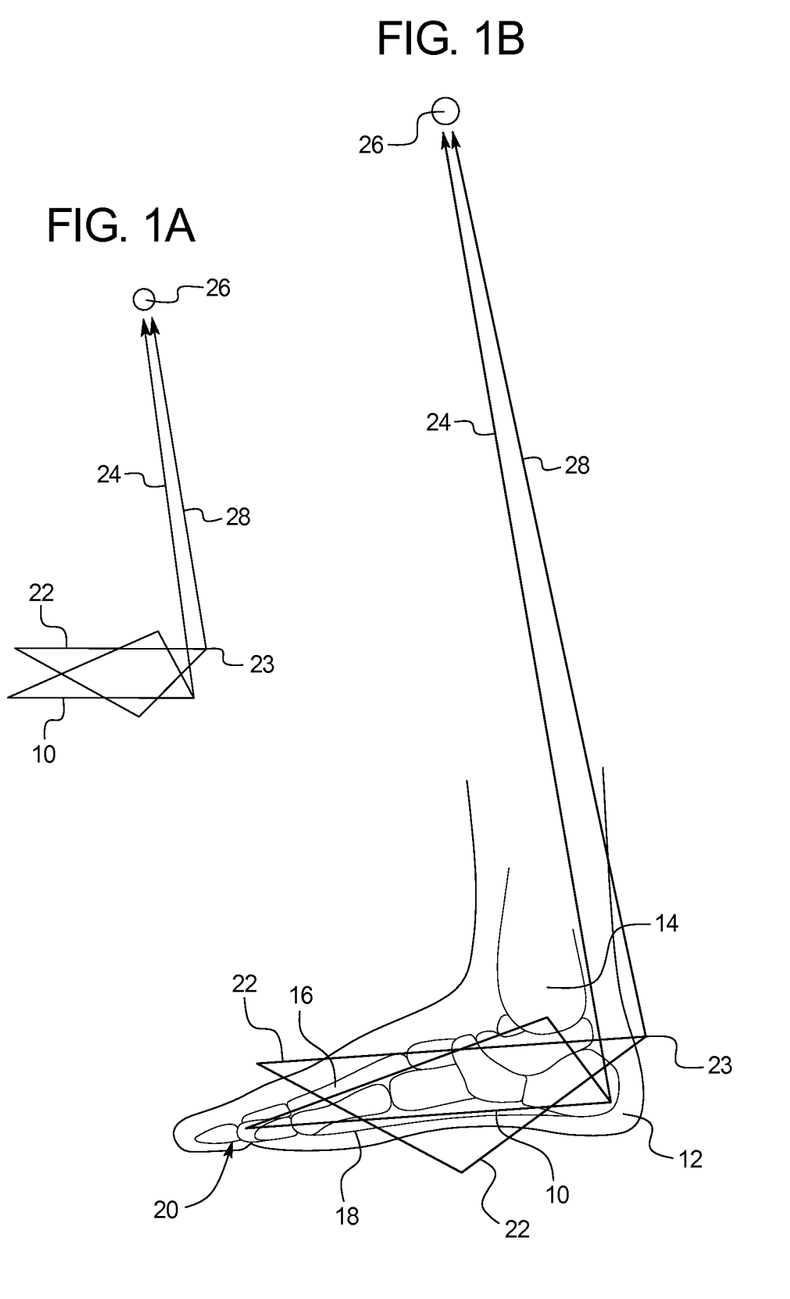
FIGS. 1a-1b are side view perspectives of a force diagram and the force diagram overlaid on a user's foot, respectively.

FIG. 1a is a force diagram that depicts a foot truss 10 of a user's foot. As depicted in FIG. 1b, the heel 12, ankle 14, and metatarsals 16 form the truss arch, while the plantar fascia 18, connecting the heel 12 to the head of the metatarsals 20, forms the base of the truss. The plantar fascia simulates a cable attached to the heel and metatarsophalangeal joints such that when the heel bone is pulled by the Achilles tendon during ambulation, the heel bone slightly rotates posteriorly and stretches the plantar fascia.

During ambulation, the foot truss 10 must tip over to enable a person to take a step forward. In order for the foot truss 10 to tip over, an increased translation force 24 must be applied to the heel end of the foot truss 10 until the heel lifts off the ground. The translation force 24 is applied to the heel end of the foot truss through the Achilles tendon to the knee joint 26. The translation force 24 increases the tension in the plantar fascia 18 until heel lift off, at which point the tension in the plantar fascia 18 is at a maximum.

FIGS. 1a-1b further depict a reverse truss 22 that is designed to limit the tension on the plantar fascia 18 by reducing the mechanical work and force required to tip over the foot truss 10 during ambulation. The reverse truss 22 reduces the tension on the plantar fascia 18 by providing an assistive force 28 from a posterior node 23 of the reverse truss 22 to the knee joint 26. The assistive force 28 reduces the translation force 24 that is responsible for the tension in the plantar fascia 18 during ambulation. Further, the reverse truss 22 by way of the assistive force 28 provides enough lift through the posterior node 23 of the reverse truss 22 to prevent hyperextension of the plantar fascia during ambulation.

Figure 2A:
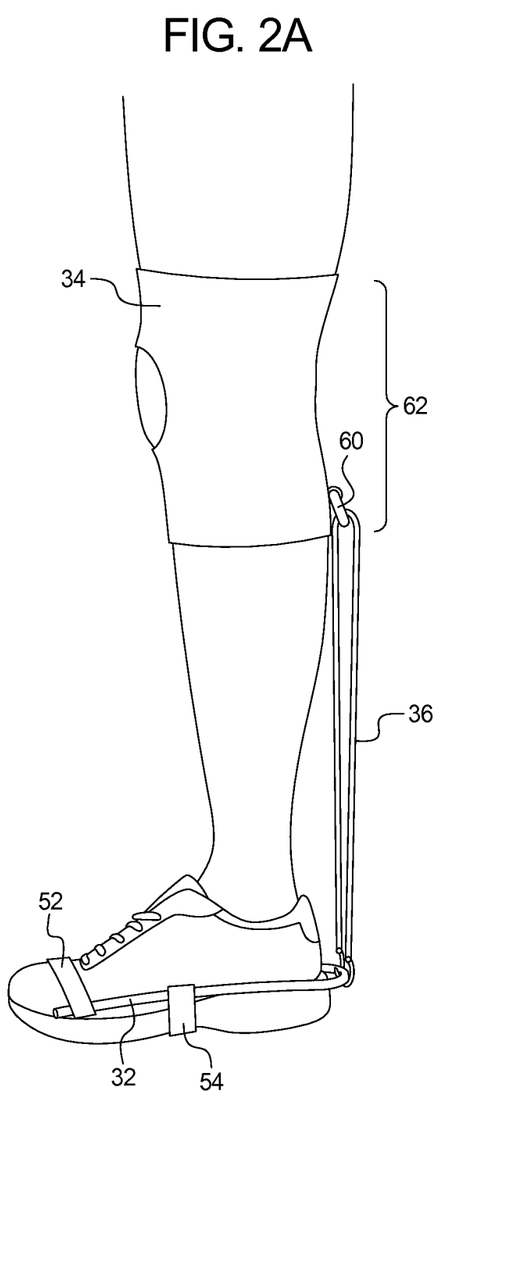
FIGS. 2a-2b are a side view and a back view perspective, respectively, of an embodiment of the device, in operative position with a user's foot.
Figure 2B:
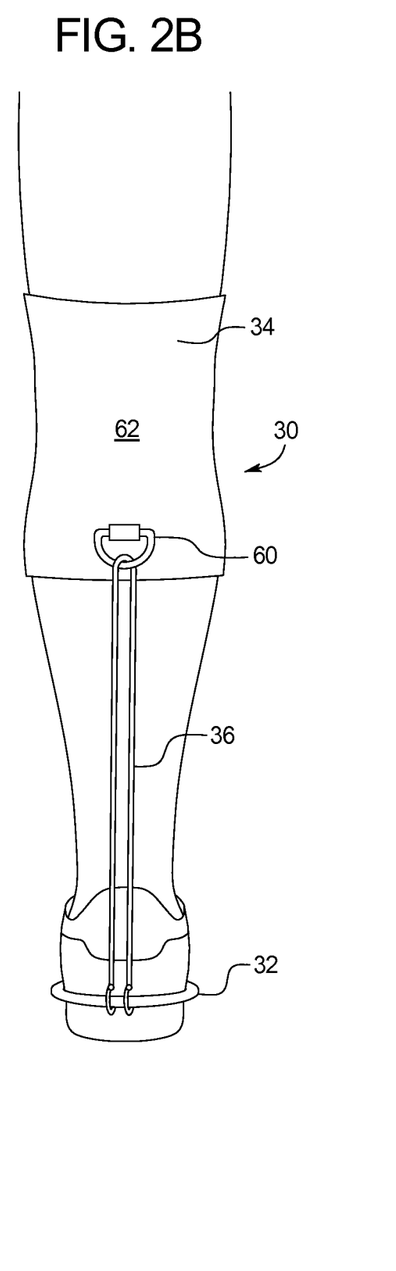

FIGS. 2a-2b illustrate a side view and back view perspective, respectively, of an embodiment of the device 30 that reduces tension in plantar fascia during ambulation, as provided herein. As shown FIGS. 2a-2b, device 30 includes a truss structure 32, an upper anchor 34, and an actuator 36.

Figure 3:
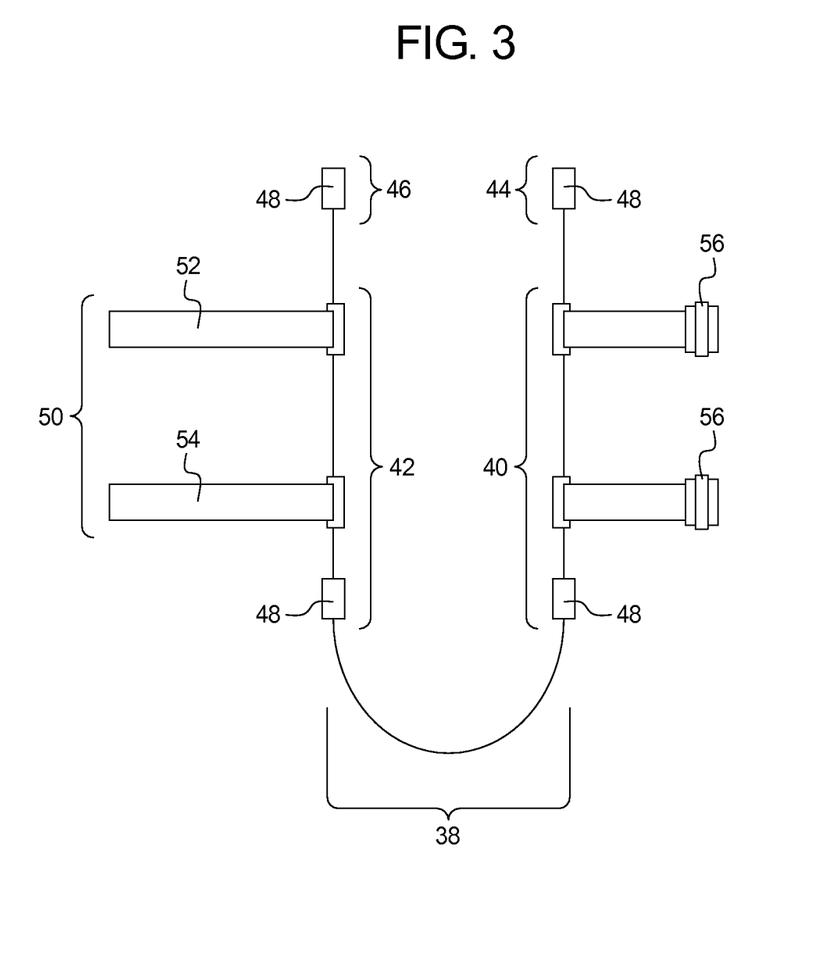
FIG. 3 is a top view perspective of an embodiment of the truss structure.

The truss structure 32, illustrated in FIG. 3, includes a posterior portion 38, a lateral portion 40, a medial portion 42, a lateral end 44, and a medial end 46. The lateral end 44 may align with the lateral metatarsophalangeal joint and the medial end 46 may align with the medial metatarsophalangeal joint of a user's foot. The alignment of the lateral end 44 and medial end 46 of the truss structure 32 to the relative metatarsophalangeal joints (the joints connecting the metatarsals to the phalanges) allows plantar fascia to maintain mobility without over extending and injuring the plantar fascia.

The truss structure 32 may be constructed from a variety of materials that result in a rigid, semi-rigid, or flexible structure. For example, the truss structure 32 may be constructed from, although not limited to, steel, iron, titanium, various metal alloys, polymeric materials, or any combinations thereof. Further, the truss structure 32 may include a hinge in the lateral portion 40 and medial portion 42 to provide additional freedom of movement of the foot during ambulation.

The truss structure 32 may further include at least one stabilizing element 48. The stabilizing element 48 may be any stabilizing mechanism that aids the truss structure in maintaining operability with a user's shoe during ambulation. Examples of a stabilizing element 48 include, but are not limited to, a grommet, clasp, hook, clamp, fastener, latch, bolt, or any combinations thereof.

Device 30 may also include a securing mechanism 50 configured to secure the truss structure 32 to a user's shoe. Examples of the securing mechanism 50 include, but are not limited to, straps, belts, ropes, elastic material, hook and loop material, or any combinations thereof. In one example, the securing mechanism 50 may extend from the lateral portion 40 of the truss structure 32 to the medial portion 42 of the truss structure 32. The securing mechanism 50 may include a fastener element 56. The fastener element 56 may be any fastener element known to those skilled in the art including buckles, pins, latches, clips, hook and loop systems (e.g., Velcro™), or combinations thereof.

The securing mechanism 50 may include at least one dorsal strap 52 that extends dorsally (over the top of a user's shoe) from the lateral portion of the truss structure 32 to the medial portion 42 of the truss structure 32, and at least one ventral strap 54 that extends ventrally (below the bottom of a user's shoe) from the lateral portion 40 of the truss structure to the medal portion 42 of the truss structure 32. The dorsal strap 52 is preferably located above the metatarsophalangeal joint, serving as a pivot point in the foot truss 10. The ventral strap 54 is preferably located at the midpoint of the reverse truss 22.

FIG. 3 depicts the dorsal strap 52 as two separate straps that are joined by a faster element 56. However, the dorsal strap 52 and the ventral strap 54 may each be a continuous strap, respectively, that joins the lateral portion 40 to the medial portion 42.

It is contemplated that the truss structure 32 may be secured to the outside of a user's shoe. Alternatively, the truss structure 32 may be configured to be inserted into a user's shoe. In addition, the truss structure 32 may be fully integrated within the structure of a user's shoe.

The truss structure 32 may further comprise a heel support to provide additional support to the plantar fascia during ambulation. For example, the posterior portion 38 of the truss structure 32 may have a cupped heel support securely connected to the posterior portion 38. The actuator 36 may be directly attached to the heel support or the posterior portion 38 of the truss structure 32.

Device 30 includes an upper anchor 34 that is proximally located a fixed or adjustable distance from the truss structure 32. For example, the upper anchor 34 may be positioned at the user's ankle, the user's calf, the user's knee joint, or above the user's knee joint, for example, at the user's lower or upper thigh. In yet another contemplated example, the upper anchor 34 may be anchored to the user's hip or waist. Additionally, the upper anchor 34 may wrap around the knee joint and also extend upward to wrap around a person's upper thigh or even waist to provide additional support. It is contemplated that the position of the upper anchor 34 is adjustable such that a user could adjust or modify the placement of the upper anchor 34 anywhere along the user's leg, hip or waist.

Figure 4:
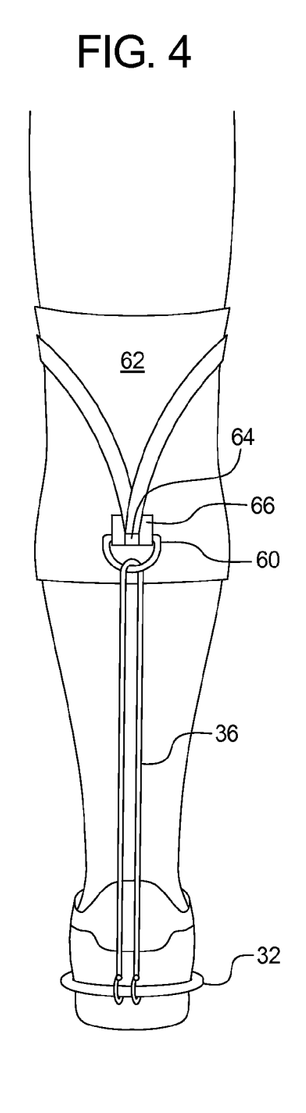
FIG. 4 is a back view perspective of an embodiment of the device, in operative position with a user's shoe.

In one example, the upper anchor 34 is configured to fit around a portion of a user's leg. For example, the upper anchor 34 may be configured to fit around a user's knee joint, for example, as a knee brace. The upper anchor 34 may comprise a connector element 60 on the posterior portion 62 of the upper anchor to secure the upper anchor 34 to the actuator 36. The connector element 60 may include any connector element known to those skilled in the art including hooks, rings, pins, latches, clips, adhesive, hook and loop systems, or combinations thereof. For example, the connector element 60 may be a D-ring that is connected directly to the posterior portion of the upper anchor 34. Alternatively, as shown in FIG. 4, a D-ring may be strapped to the upper anchor with a hook and loop material to allow a variable positioning of the D-ring and to allow the force of the actuator to spread around the knee joint. In one embodiment, the D-ring may be sewn or otherwise integrated into the upper anchor 34.

The upper anchor 34 may be constructed of various materials. In one example, the upper anchor 34 may be a conventional knee brace. Alternatively, the upper anchor 34 may be constructed from injection molded plastics, metal, carbon fiber, various fabrics, or combinations thereof.

The device 30 includes an actuator 36 that couples the posterior portion 38 of the truss structure 32 to a posterior portion of the upper anchor 62. The actuator 36 is designed to provide assistive force 28 to urge heel lift during ambulation such that the tension in the plantar fascia is reduced. At heel lift, the maximum tension in the plantar fascia is attenuated because the actuator 36 transmits some of the force applied to the plantar fascia towards the upper anchor 34. As a result, the tension in the plantar fascia is reduced which allows the plantar fascia to heal with reduced risk of re-injury during ambulation.

The actuator 36 may be made of any material that provides adequate assistive force 28 to urge heel lift during ambulation. The actuator 36 may be a mechanical, electromechanical or elastic actuator. In addition, the actuator 36 may be calibrated to apply a range of assistive force magnitudes. The actuator 36 may include elastic material, non-elastic material, a spring, or combinations thereof. The length of the actuator 36 is such to provide adequate tension to the truss structure 32 to relieve tension in the plantar fascia during ambulation.

Figure 5:
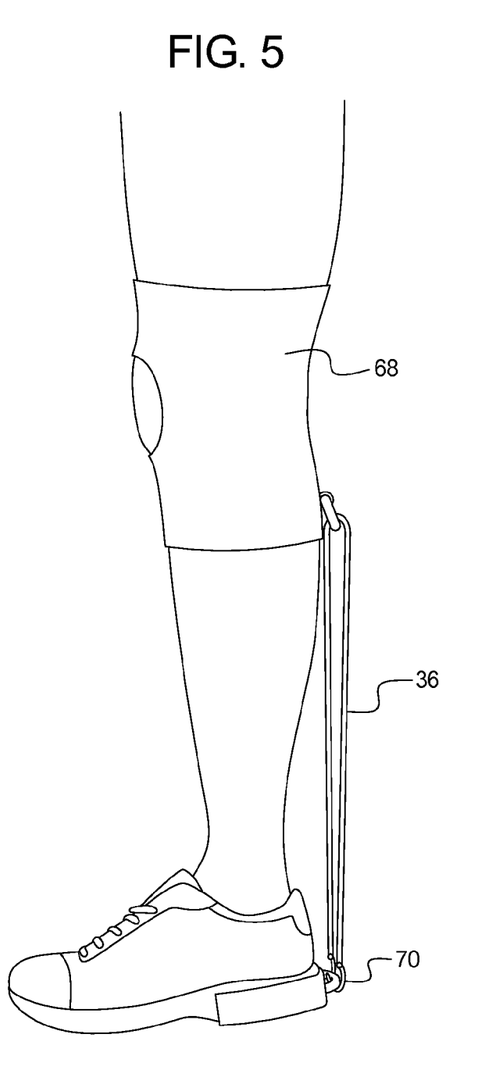
FIG. 5 is a side view perspective of an embodiment of the device, in operative position with a user's foot.

The actuator 36 may be attached to the posterior portion 38 of the truss structure 32 and to a posterior portion 62 of the upper anchor 34 by any connecting mechanism known to one skilled in the art. For example, as shown in FIGS. 2a-2b, the actuator 36 is connected to the posterior portion 38 of the truss structure 32 by an S-hook, the actuator 36 is then threaded through a D-ring on the posterior portion 62 of the upper anchor 34, and then the actuator 36 is secured again to the posterior portion 38 of the truss structure 32 by an S-hook. Alternatively, as shown in FIG. 5, the actuator 36 may be connected to the posterior portion 38 of the truss structure 32 by an S-hook and directly connected to a posterior portion 62 of the upper anchor 34 by an S-hook.

The actuator 36 may further include a tension sensor 64, as shown in FIG. 4, enabled to determine the amount of assistive force provided by the actuator 36 on the truss structure 32. The tension sensor 64 may be wirelessly or otherwise connected to a computing device that can calculate the mechanical work being performed by a user's foot.

The actuator 36 may further include a tension adjustment mechanism 66. The tension adjustment mechanism 66 may be any tension adjustment means that is known by those skilled in the art. For example, the tension adjustment mechanism 66 may be a manual tension adjustment mechanism or an automatic tension adjustment mechanism.

The manual tension adjustment mechanism may include modifying the position of the upper anchor 34, the position of the connector element 60 of the upper anchor, or the position of the posterior portion 38 of the truss structure 32. Alternatively, or in addition to, the manual tension adjustment mechanism may include modifying the tension provided by the actuator 36. For example, the manual tension adjustment mechanism may include tightening or loosening straps securing a connector element 60, such as a D-ring, to the posterior portion 62 of the upper anchor to vary the provided tension. The manual tension adjustment mechanism may include replacing the actuator 36 with a different actuator that provides more or less tension.

The automatic tension adjustment mechanism may include an electrical system for modifying the assistive force provided by the actuator 36. It is contemplated that the tension sensor 64 may be cooperatively connected to the automatic tension adjustment mechanism. For example, if the tension sensor 64 indicates the assistive force is too high or too low, the automatic tension adjustment mechanism automatically adjusts the assistive force provided by the actuator 36 to yield an assistive force that is in an optimal and comfortable range for supporting the plantar fascia.

In an embodiment, the device 30 includes an upper anchor, which in the embodiment illustrated in FIG. 5 is brace 68, adapted to be secured to a user's leg at the user's ankle up to beneath the user's hip and an attachment point 70 adapted to be secured adjacent to the posterior portion of a user's heel. The actuator 36 couples the brace 68 to the attachment point 70, such that the actuator 36 pulls the attachment point 70 towards the brace 68.

The attachment point 70 may be any connecting mechanism that is known by one skilled in the art. Examples of the attachment point 70 include, but not limited to, a hook, bracket, latch, ring, loop, or any combination thereof. Further, the attachment point 70 may be a portion of the truss structure 32. Alternatively, the attachment point 70 may be integrated into a user's shoe, as shown in FIG. 5.

The present disclosure also provides a method of mitigating plantar fasciitis including providing device 30 disclosed herein, associating the truss structure 32 with a user's shoe, inserting a user's foot into the shoe, and securing the upper anchor to a user's leg. The method includes the actuator 36 urging heel lift during ambulation, thereby relieving tension in the plantar fascia.

The method disclosed herein may be used to not only treat plantar fasciitis but also a wide range of conditions that originate with compromised foot or ankle activity, such as Achilles tendonitis.

It should be noted that various changes and modifications to the embodiments described herein will be apparent to those skilled in the art. Such changes and modifications may be made without departing from the spirit and scope of the present invention and without diminishing its attendant advantages. For example, various embodiments of device 30 may be provided based on various combinations of the features and functions from the subject matter provided herein.

I claim:

1. A device that reduces tension in a plantar fascia during ambulation comprising:
    a truss structure comprising a posterior portion, a lateral portion, a medial portion, a lateral end, and a medial end;
    an upper anchor proximally located from the truss structure; and
    an actuator coupling the posterior portion of the truss structure to a posterior portion of the upper anchor;
    wherein the truss structure further comprises at least one securing mechanism that extends from the lateral portion of the truss structure to the medial portion of the truss structure, wherein the securing mechanism secures the truss structure to a user's shoe; and
    wherein the securing mechanism comprises at least one dorsal strap that extends dorsally from the lateral portion of the truss structure to the medial portion of the truss structure, and at least one ventral strap that extends ventrally from the lateral portion of the truss structure to the medial portion of the truss structure.

2. The device of claim 1 wherein the truss structure further comprises at least one stabilizing element that aids the truss structure in maintaining operability with a user's shoe during ambulation.

3. The device of claim 1 wherein
    the lateral end of the truss structure aligns with a lateral metatarsophalangeal joint of a user's foot, and
    the medial end of the truss structure aligns with a medial metatarsophalangeal joint of a user's foot.

4. The device of claim 1 wherein the truss structure is integrated within a user's shoe.

5. The device of claim 1 wherein the truss structure is inserted into a user's shoe.

6. The device of claim 1 wherein the posterior portion of the truss structure comprises a heel support.

7. The device of claim 1 wherein the upper anchor comprises a connector element to secure the upper anchor to the actuator.

8. The device of claim 1 wherein the upper anchor is configured to fit around a portion of a user's leg.

9. The device of claim 1 wherein the actuator provides tension to urge heel lift during ambulation.

10. The device of claim 1 wherein the actuator comprises a non-elastic material.

11. The device of claim 1 wherein the actuator comprises an elastic material.

12. The device of claim 1 wherein the actuator comprises an electromechanical actuator.

13. The device of claim 1 wherein the truss structure allows mobility of the metatarsophalangeal joint during ambulation.

14. The device of claim 1 wherein the actuator further comprises a tension sensor enabled to determine the amount of tension provided by the actuator on the truss structure.

15. The device of claim 1 wherein the actuator further includes a tension adjustment mechanism.

16. A method of mitigating plantar fasciitis comprising:
    providing a device that reduces tension in a plantar fascia during ambulation comprising,
        a truss structure comprising a posterior portion, a lateral portion, a medial portion, a lateral end, and a medial end,
        an upper anchor proximally located from the truss structure, and
        an actuator coupling the posterior portion of the truss structure to a posterior portion of the upper anchor;
    associating the truss structure with a user's shoe;
    inserting a user's foot into the shoe; and
    securing the upper anchor to a user's leg.

17. The method of claim 16 wherein the actuator urges heel lift during ambulation.

18. The method of claim 16 wherein the upper anchor is configured to fit around a portion of a user's leg.

19. A device comprising:
    an upper anchor adapted to be secured to a user's leg;
    an attachment point adapted to be secured adjacent to the posterior portion of the user's heel;
    an actuator coupling the upper anchor to the attachment point, wherein the actuator pulls the attachment point towards the upper anchor; and
    a truss structure comprising a posterior portion, a lateral portion, a medial portion, a lateral end, and a medial end;
    wherein the truss structure further comprises at least one securing mechanism that extends from the lateral portion of the truss structure to the medial portion of the truss structure, wherein the securing mechanism secures the truss structure to a user's shoe; and wherein the securing mechanism comprises at least one dorsal strap that extends dorsally from the lateral portion of the truss structure to the medial portion of the truss structure, and at least one ventral strap that extends ventrally from the lateral portion of the truss structure to the medial portion of the truss structure.

20. The device of claim 19 wherein the attachment point is integrated into a shoe.

21. The device of claim 19 wherein the attachment point is a portion of the truss structure adapted to be secured to a shoe.

22. The device of claim 19 wherein the upper anchor is a brace configured to fit around a user's knee.

* * * * *